US008623397B2

(12) United States Patent
Ma et al.

(10) Patent No.: US 8,623,397 B2
(45) Date of Patent: Jan. 7, 2014

(54) DELIVERY DEVICE AND METHOD FOR FORMING THE SAME

(75) Inventors: Peter X. Ma, Ann Arbor, MI (US);
Xiaohua Liu, Ann Arbor, MI (US);
Laurie McCauley, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 591 days.

(21) Appl. No.: 12/101,993

(22) Filed: Apr. 13, 2008

(65) Prior Publication Data

US 2008/0254095 A1    Oct. 16, 2008

Related U.S. Application Data

(60) Provisional application No. 60/911,606, filed on Apr. 13, 2007.

(51) Int. Cl.
*A61F 2/00* (2006.01)
*B29C 33/40* (2006.01)
*A01N 61/00* (2006.01)
*A61K 39/00* (2006.01)

(52) U.S. Cl.
USPC ............. 424/426; 264/221; 514/1; 424/184.1

(58) Field of Classification Search
None
See application file for complete search history.

(56) References Cited

U.S. PATENT DOCUMENTS

| | | | |
|---|---|---|---|
| 5,011,692 A * | 4/1991 | Fujioka et al. | 424/426 |
| 5,320,853 A | 6/1994 | Noda et al. | |
| 5,474,786 A | 12/1995 | Kotwal et al. | |
| 5,618,560 A * | 4/1997 | Bar-Shalom et al. | 424/486 |
| 2004/0082937 A1 * | 4/2004 | Ausiello et al. | 604/891.1 |
| 2005/0008690 A1 * | 1/2005 | Miller | 424/451 |

FOREIGN PATENT DOCUMENTS

| | | |
|---|---|---|
| WO | WO 88/08299 | 11/1988 |
| WO | WO 95/01781 | 1/1995 |
| WO | WO 99/08662 | 2/1999 |
| WO | WO 03/000237 * | 1/2003 |
| WO | WO 2004/064815 | 8/2004 |

OTHER PUBLICATIONS

BOne MEdical, Oral Paratheyroid Hormone BN003, p. 1, 2004.*
Polymer, Wikipedia, date accessed: Nov. 10, 2011, pp. 1-16.*
International Search Report for S.N. PCT/US2008/060161 dated Aug. 13, 2008 (14 pages).
International Preliminary Report on Patentabity for International Appln. No. PCT/US2008/060161 dated Oct. 22, 2009 (8 pages).
Bussemer, T., et al., "A pulsatile drug delivery system based on rupturable coated hard gelatin capsules", Journal of Controlled Release 93, Dec. 2003, pp. 331-339.
Chen, V. J., et al., "Bone regeneration on computer-designed nano-fibrous scaffolds", Biomaterials 27, Jul. 2006, pp. 3973-3979.
Grayson, A. C. R., et al., "Multi-pulse drug delivery from a resorbable polymeric microchip device", Nature Materials, vol. 2, Nov. 2003, pp. 767-772.
Hou, S. J., et al., "Synthesis and erosion properties of PEG-containing polyanhydrides", Macromolecule Bioscience, vol. 7, 2007, pp. 620-628.
Isakov, R. M., et al., "Time-programmed pulsatile release of dextran from calcium-alginate gel beads coated with carboxy-n-propylacrylamide copolymers", Journal of Controlled Release 80, Apr. 2002, pp. 57-68.
Jiang, H. L., et al., "Pulsatile protein release from a laminated device comprising of polyanhydrides and pH-sensitive complexes", International Journal of Pharmaceutics 194, Jan. 2000, pp. 51-60.
Jimoh, A. G., et al., "Pulsed FSH release from an implantable capsule system", Journal of Controlled Release 34, May 1995, pp. 87-95.
Krogel, I., et al., "Pulsatile drug release from an insoluble capsule body controlled by an erodible plug", Pharmaceutical Research 15, Mar 1998, pp. 474-481.
Santini, J. T., et al., "A controlled-release microchip", Nature, vol. 397, Jan. 1999, pp. 335-338.
Wei, G. B., et al., "The release profiles and bioactivity of parathyroid hormone from poly(lactic-co-glycolic acid) microspheres", Biomaterials 25, Jan. 2004, pp. 345-352.

* cited by examiner

*Primary Examiner* — Scott Long
*Assistant Examiner* — Lyndsey Beckhardt
(74) *Attorney, Agent, or Firm* — Dierker & Associates, P.C.

(57) ABSTRACT

A delivery device includes a hollow container, and a plurality of biodegradable and/or erodible polymeric layers established in the container. A layer including a predetermined substance is established between each of the plurality of polymeric layers, whereby degradation of the polymeric layer and release of the predetermined substance occur intermittently. Methods for forming the device are also disclosed herein.

15 Claims, 6 Drawing Sheets

0 PEG

FIG. 3A 2.5 PEG

FIG. 3B 7.5 PEG

DELIVERY DEVICE AND METHOD FOR FORMING THE SAME

CROSS-REFERENCE TO RELATED APPLICATIONS

This application claims the benefit of U.S. Provisional Patent Application Ser. No. 60/911,606 filed Apr. 13, 2007, which is incorporated herein by reference in its entirety.

STATEMENT REGARDING FEDERALLY SPONSORED RESEARCH OR DEVELOPMENT

This invention was made in the course of research partially supported by a grant from the National Aeronautics and Space Administration (NASA) Bioscience and Engineering Institute, Grant No. NNC04AA21A, and from the National Institutes of Health (NIH) and the National Institute of Dental and Craniofacial Research (NIDCR), Grant No. DE015384. The U.S. government has certain rights in the invention.

BACKGROUND

The present disclosure relates generally to delivery devices and a method for forming the same.

Parathyroid hormone (PTH) is a peptide hormone that is capable of exhibiting either anabolic or catabolic effects on bone, depending, at least in part, on the dosage and delivery pattern. Generally, a continuous high dose delivery of PTH leads to catabolic effects, while a continuous low dose or a pulsatile high dose delivery of PTH results in anabolic effects on bone. Daily injections may be an anabolic treatment, however, such treatment is less convenient and may not be favorable to patients. As such, controlled delivery of PTH, and other like substances, in an anabolic fashion is highly desirable.

Attempts have been made to devise a successful system for pulsatile substance release. Such systems may be classified as stimulus-induced pulsatile release systems or self-regulated pulsatile release systems. In stimulus-induced delivery systems, drugs are triggered to release by external stimuli, such as temperature, pH, light, enzymes, electric and magnetic fields, and/or combinations thereof. While these stimulus-responsive devices have shown promising pulsatile release characteristics, many of the stimuli are not suitable or preferable for use in patients. In addition, most of the systems in this category are constructed using non-biodegradable polymers.

In self-regulated pulsatile release systems, drugs are usually encapsulated within a barrier material, which is often composed of an erodible or biodegradable polymer. After the barrier material is dissolved, eroded or degraded, the drugs are rapidly released from the inner reservoir core. These systems are usually biocompatible and biodegradable, but multiple barriers or coatings may be required to achieve the desired multiple pulses of release. Multiple layers may, however, pose challenges in material properties and device fabrication technologies, often resulting in inconsistency.

Other attempts to devise a successful system for pulsatile substance release have included combining the self-regulated release reservoir design with a microfabrication technique. Disk-shaped biodegradable polymeric chips have been fabricated to achieve multi-pulse drug release. While this device may be useful, the reservoirs in the device are arranged parallel to each other, which potentially wastes space and limits the miniaturization capacity.

SUMMARY

A delivery device includes a hollow container, and a plurality of biodegradable and/or erodible polymeric layers established in the container. A layer including a predetermined substance is established between each of the plurality of polymeric layers, whereby degradation of the polymeric layers and release of the predetermined substance occur intermittently. A method for forming the device is also disclosed herein.

BRIEF DESCRIPTION OF THE DRAWINGS

Features and advantages of embodiments of the present disclosure will become apparent by reference to the following detailed description and drawings, in which like reference numerals correspond to the same or similar, though perhaps not identical, components. For the sake of brevity, reference numerals having a previously described function may or may not be described in connection with subsequent drawings in which they appear.

FIGS. 1A through 1F depict a primarily perspective schematic illustration of an embodiment of a fabrication process of an implantable pulsatile delivery system, where FIG. 1E is shown as a cross section of FIG. 1F taken along the 1E-1E line;

DETAILED DESCRIPTION

Embodiments of the delivery device disclosed herein include a biodegradable polymer system with tunable erosion properties to enable controlled pulsatile release of one or more substances. The intervals between the pulses may be the same or different, and may advantageously be tailored for specific needs. Furthermore, the device may be configured in a variety of different ways, for example, to release the same substance over different pulses, to release a different substance or multiple substances at each pulse, to release the same or different amounts of the substance at least pulse, or combinations thereof.

Such devices may be suitable for systemic and for local therapies. The device disclosed herein is biocompatible, and may be implanted in humans and animals to deliver therapeutics or other agents. As non-limiting examples, the device disclosed herein may be configured for osteoporosis treatment, bone regeneration, defective tissue treatment, ovulation induction, treatment of vasomotor symptoms, treatment of urogenital symptoms, endometrial hyperplasia treatment, allergic rash treatment, eczema treatment, and/or the like, and/or combinations thereof.

Figure 1A:
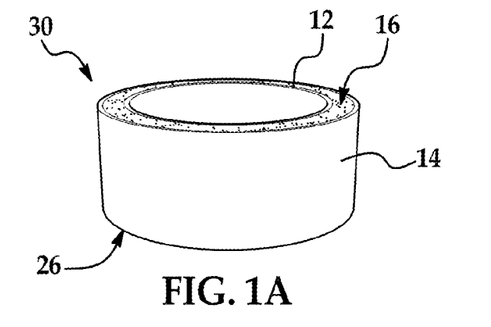
Figure 1B:
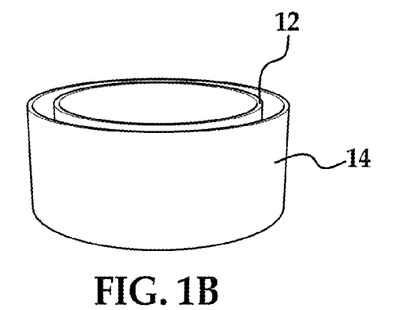
Figure 1C:
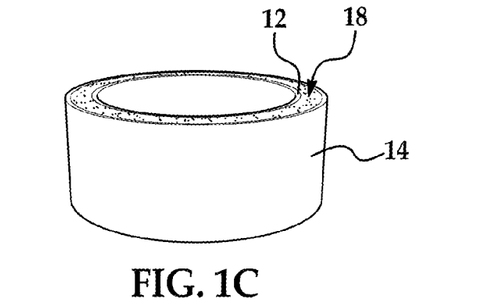
Figure 1D:
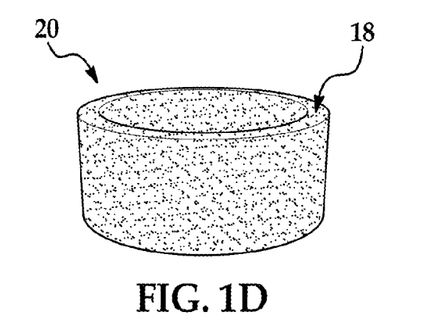
Figure 1E:
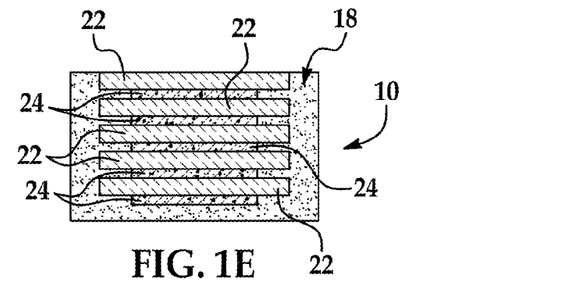
Figure 1F:
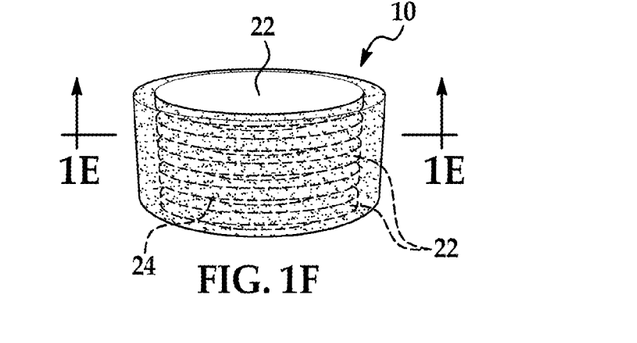

Referring now to FIGS. 1A through 1F, an embodiment of the method for forming an embodiment of the device 10 (see FIG. 1E (a cross-sectional view) and FIG. 1F (a perspective view) is shown. Very generally, the method includes providing a hollow container 20 (FIG. 1D), and establishing alternating layers of a biodegradable and/or erodible polymer 22 and a predetermined substance 24 in the hollow container 20. In an embodiment, each of the alternating polymeric layers is a surface-erosion polymer.

FIGS. 1A through 1D together depict the formation of the hollow container 20. In an embodiment, the hollow container 20 is formed using a reverse solid free form fabrication technique. As shown in FIG. 1A, a mold 30 having a desired shape for the hollow container 20 is formed having a bottom 26, an interior layer 12, an exterior layer 14 and an intermediate layer 16 between the layers 12, 14. The configuration of the mold 30 (and the formed container 20) may have any desirable size and/or shape. In an embodiment, the mold 30 and container 20 are substantially cylindrical. Generally, the thickness of the intermediate layer 18 is equal to the distance of the space between the layers 12, 14 of the mold 30.

In an embodiment, the design of the mold 30 is created and converted into a stereolithography (STL) file using, for example, Rhinoceros software (Robert McNeel & Associates, Seattle, Wash.), and then imported into, for example, Modelworks software (Solidscape) to convert the file for three-dimensional (3D) printing. The mold 30 may be printed from two nozzles in a layer-by-layer fashion using a rapid prototyping machine (Modelmaker II, Solidscape). In a non-limiting example, different colored waxes may be used to form the layers 12, 14 and the intermediate layer 16. This enables one to easily distinguish the multiple layers 12, 14, 16 of the mold 30.

The computer-assisted design (CAD) and reverse solid free form fabrication technique may advantageously aid the accurate fabrication of devices 10 having various shapes and sizes, thereby ensuring repeatability of the manufacturing process.

After the mold 30 is printed, a solvent (e.g., ethanol) may be used to dissolve the intermediate layer 16 (shown in FIG. 1B). It is to be understood that the solvent is selected such that it dissolves the intermediate layer 16, but does not dissolve layers 12, 14. As such, the solvent selected will depend, at least in part, on the material used for the intermediate layer 16 and the materials used for the layers 12, 14. Furthermore, the materials used for layers 12, 14 may be different from that used for layer 16 so that selective dissolution of layer 16 is achievable. As shown in FIG. 1C, the space from which the intermediate layer 16 is removed may be filled with a solution of a material 18 that will form the container 20. The material 18 may be any material that maintains its structural integrity prior to completion of substance release from the device 10. In an embodiment, the material 18 is poly(L-lactide) (PLLA). Non-limitative examples of other suitable materials 18 include polymeric materials selected from natural or synthetic polymers, degradable polymers, non-degradable polymers, or partially degradable polymers, proteins, polysaccharides, hydrocarbon polymers, artificial proteins, and combinations thereof. More specific non-limitative examples include poly(lactide-co-glycolide) (PLGA), polyglycolic acid (PGA), polyanhydrides, poly(ortho ethers), polycaprolactone, poly(hydroxy butyrate), poly(phosphoesters), poly (propylene fumarate), polyphosphazenes, polycarbonates, polyethylene, polyurethane, copolymers thereof, and/or combinations thereof. PLLA may be particularly suitable because of its biocompatibility and biodegradability, as well as its good mechanical properties. Such a material may be advantageous in that there is no need for retrieval of empty devices 10 after the completion of substance release.

This material solution 18 may be cast into the mold 30, whereby the material solution 18 takes the shape of the original intermediate layer 16. The material solution 18 is allowed to dry.

As shown in FIG. 1D, the remaining mold 30 (interior layer 12, exterior layer 14, and bottom 26) is removed, leaving hollow container 20. The process by which the mold 30 is removed, depends, at least in part, on the material used to form the mold 30. In an embodiment, the mold 30 is removed by dissolution. The container 20 may be washed, dried, and stored, as desired.

FIG. 1E depicts the incorporation of the layers 22, 24 into the container 20. Prior to such incorporation, the layers 22, 24 are formed. The polymer layer 22 (also referred to herein as isolation layer 22) may be a copolymer of a sebacic acid anhydride precursor, a 1,3-bis(carboxyphenoxy) propane anhydride precursor, and a poly(ethylene glycol) anhydride precursor. Non-limiting examples of these copolymers and methods of forming the same are discussed in U.S. Provisional Patent Application No. 60/794,617, filed on Apr. 25, 2006, incorporated by reference herein. The PEG segments are incorporated into polyanhydride copolymers, at least in part, to modulate the erosion rate and to improve processing properties of the polyanhydride films/layers 22. With increasing PEG content, the polyanhydride erosion rate increases. Without being bound to any theory, it is believed that the structural tunability of such polyanhydrides will advantageously enable a broad range of lag times (between substance release) and various device 10 sizes.

Other non-limiting examples of suitable isolation layers 22 include polymeric materials selected from natural or synthetic degradable polymers, proteins, polysaccharides, hydrocarbon polymers, artificial proteins, and/or combinations thereof. Specific non-limiting examples include poly (lactide-co-glycolide) (PLGA), polyglycolic acid (PGA), poly(L-lactic acid) (PLLA), polyanhydrides, poly(ortho ethers), polycaprolactone, poly(hydroxy butyrate), poly(phosphoesters), poly(propylene fumarate), polyphosphazenes, polycarbonates, polyurethane, copolymers thereof, and/or combinations thereof.

To form the layer 22, the selected polymer(s) is/are heated until melted. The polymeric melt is then cooled down (e.g., to room temperature) and compressed into films of a desirable thickness. It is to be understood that the composition and/or thickness selected for the layer 22 depends, at least in part, on the desirable release characteristics (lag time and release pattern) for the device 10. Upon formation, the layer 22 may be divided into any desirable shape for incorporation into the container 20.

The layer 24 including the predetermined substance may be formed by mixing the predetermined substance with a film forming material to form a solution, and casting the solution onto a removable substrate. Non-limiting examples of the film forming material include polymeric materials selected from natural or synthetic hydrophilic polymers, natural or synthetic amphophilic polymers, proteins, polysaccharides, hydrocarbon polymers, lipids, artificial proteins, and/or combinations thereof. More specific non-limitative examples include alginate, PEG, collagen, gelatin, hyaluronic acid, starch, glycogen, cellulose, caragena, dextran, chitin, chitosan, pectin, heparan, heparan sulfate, copolymers thereof, small water soluble molecules (such as sugars, salts), and combinations thereof. It is believed that alginate may be particularly suitable as a carrier for the selected substance, in part, because of its biocompatibility and suitable processing properties.

The solution is dried to form the substance layer 24, which may be removed from the substrate and divided into any desirable shape for incorporation into the container 20. N Non-limiting examples of suitable substances that are incorporated into layer 24 include drugs, vaccines, proteins, peptides, growth factors, hormones (e.g., PTH, luteinizing hormone release hormone (LHRH), 17β-estradiol, estriol, progesterone, testosterone, cortisol, etc.), DNAs, RNAs, other biological molecules, non-biological molecules, and/or combinations thereof. The thickness and substance content of the layer 24 may be selected, at least in part, on the desirable amount of substance to be released and the release time.

As shown in FIG. 1E, the layers 22, 24 are formed into disks having a shape configured to be introduced into the container 20. In an embodiment, each of the polymeric layers 22 has an area that is equal to or larger than an area of each of the predetermined substance layers 24.

The inner portion of the container 20 may be pre-wet with a desirable liquid (e.g., ethanol), and the layers 22, 24 are alternately introduced into the container 20.

It is to be understood that the layers 24 including the predetermined substance may be the same or different throughout the device 10. For example, the substance loading may be higher in some layers 24 than in others 24, or the type of substance may be different in two or more layers 24. In a non-limiting example, the amount of substance loaded in each layer 24 is 50% higher than the substance loading in the layer 24 immediately above, in part, to overcome the potential adsorption and diffusive losses of the released substance in lower layers 24.

Once the layers 22, 24 are established in the container 20, the device 10 may be compressed under pressure for a predetermined time. Additional material (which may be the same as or different from the material 18 used to form the container 20) may be added to the device 10 to fill any spaces between loaded layers 22, 24, and any gaps between the stacked layers 22, 24 and the container 20. In an embodiment, the additional material seals the layers 22, 24 in the device 10.

The device 10 may be air purged for a predetermined time to accelerate solvent evaporation. The device 10 may also be dried for a predetermined time.

Figure 2:
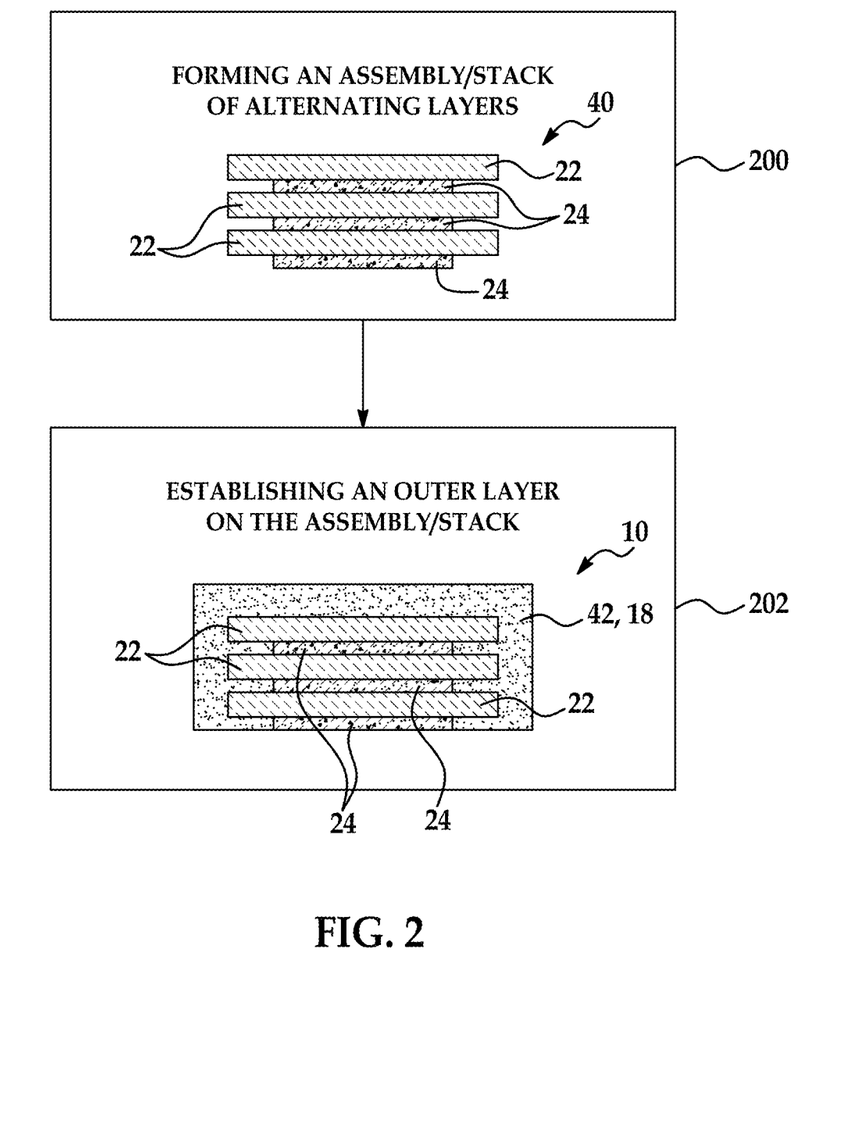
FIG. 2 is a schematic and cross-sectional flow diagram depicting another embodiment of a fabrication process of an implantable pulsatile delivery system.

FIG. 2 depicts another embodiment of the device 10 fabrication method. Generally, the method includes forming an assembly or stack 40 of the alternating layers 22, 24, as shown at reference numeral 200, and then establishing an outer layer 42 on the assembly/stack 40 of layers 22, 24, as shown at reference numeral 202. The assembly 40 may be formed by stacking a desirable number of layer 22, 24 discs, which may be formed via the methods disclosed hereinabove. In another embodiment, the layers 22, 24 may be stacked, and then the stack 40 may be configured into a desirable shape.

The outer layer 42 acts as a container 20 for the assembly/stack 40 of layers 22, 24 (similar to FIG. 1E). The outer layer 42 may be made up of material 18. In some instances, the outer layer 42 is coated over the stack 40, and in other instances, the outer layer 42 is a pre-formed hollow container (such as container 20, described hereinabove) that receives the assembly/stack 40.

When the outer layer 42 is coated on the stack 40, any suitable deposition process may be used, including, but not limited to dip coating, spaying, or wrapping with a pre-fabricated film or sheet. It is to be understood that such coating processes enable the material of the outer layer 42 to conform to the layers 22, 24. The outer layer 42 may be deposited to completely encapsulate the assembly 40, or it may be deposited such that one of the layers 22, 24 in the assembly 40 remains exposed (as shown in FIG. 2). The positioning and thickness of the outer layer 42 depends, at least in part, on the desirable release characteristics for the device 10. For example, if immediate release of the substance in layer 24 is desirable, outer layer 42 will not be deposited on the outermost layer 24 of the stack 40.

When the pre-formed hollow container 20 is used as the outer layer 42, it is to be understood that the shape/configuration of the container 20 is selected or configured such that the interior hollow portion is able to receive the stack 40. The stack 40 may also be configured during fabrication to fit into a desirable container 20. It is to be understood that an additional material (which may be the same as or different from the material 18 used to form the outer layer 42/container 20) may be added to the device 10 to fill any spaces between the layers 22, 24 of the stack 40, and any gaps between the stack 40 and the outer layer 42.

It is to be understood that either layer 22 or 24 may form the outermost layer, for example, as shown in FIG. 1E (layer 22 is the outermost layer of the stack) or in FIG. 2 (layer 24 is the outermost layer of the stack). Yet further, it is to be understood that the outermost layer may be formed of a temporary protective layer configured to dissolve away after implantation.

To further illustrate embodiment(s) of the present disclosure, an example is given herein. It is to be understood that this example is provided for illustrative purposes and is not to be construed as limiting the scope of the disclosed embodiment(s).

EXAMPLE

Embodiments of the delivery device 10 disclosed herein were fabricated. Some of devices 10 included isolation layers 22 of three-component polyanhydrides, and layers 24 with parathyroid hormone or bovine serum albumin as the predetermined substance. The three component polyanhydride isolation layers 22 were composed of sebacic acid (SA), 1,3-bis (p-carboxyphenoxy) propane (CPP), and poly(ethylene glycol) (PEG). These layers 22 were synthesized and characterized by NMR, GPC and FTIR. Lyophilized parathyroid hormone, PTH(1-34), was obtained from Bachem Bioscience Inc. (Torrance, Calif.), and bovine serum albumin (BSA, Fraction V) was purchased from Sigma (St. Louis, Mo.). Poly(L-lactic acid) (PLLA), with an inherent viscosity of approximately 1.6, was purchased from Boehringer Ingelheim (Ingelheim, Germany) and was used to form the container 20. Sodium alginate was obtained from Pronova Biopolymer (Drammen, Norway), and dichloromethane and 1,4-dioxane were purchased from Aldrich Chemical Company (Milwaukee, Wis.).

Scanning Electron Microscopy (SEM) Examination of Erosion

Rod-shaped polyanhydride specimens (2 mm in diameter and 4 mm in length) with various chemical compositions were placed in LoBind tubes (Eppendorf AG, Germany) containing 1.0 ml of phosphate buffered saline (PBS, 0.1 M, pH 7.4). The tubes were kept in an incubator at 37° C. for 24 h. The specimens were then removed and vacuum-dried for 24 h. The specimens were cross-sectioned, gold-coated and examined with scanning electron microscopy (SEM, Philips XL30 FEG) at 10 kV.

Device Frame Design and Fabrication

A cylindrical mold (3.2 mm in inner diameter, and 3.7 mm in outer diameter) with one end sealed was designed and converted into a stereolithography (STL) file using Rhinoceros software (Robert McNeel & Associates, Seattle, Wash.). The STL file was imported into Modelworks software (Solidscape) to convert the file for 3D printing. To build the mold, red wax and green wax were printed from two nozzles in a layer-by-layer fashion using a rapid prototyping machine (Modelmaker II, Solidscape) (FIG. 1A).

After the cylindrical mold was printed, ethanol was used to dissolve the green wax of the mold (FIG. 1B). A PLLA solution (10% wt/v) was cast into the mold (taking the shape of the original green material), and was air dried for 3 days (FIG. 1C). The mold containing the polymer was washed in 37° C. cyclohexane to dissolve the red wax mold (FIG. 1D). The obtained PLLA cylinder was then washed with ethanol and water, and subsequently air-dried. The PLLA cylinder was stored in a desiccator before use.

Fabrication of PTH, BSA and Polyanhydride Films

PTH films: PTH (1-34) (0.3 mg) and alginate (250 mg) were mixed and dissolved in 8 ml Milli-Q water (18.2 MΩ·cm) at 4° C. The solution was cast on a hexagonal polystyrene weigh boat (Fisher Scientific, USA), and vacuum dried at 4° C. for about 2 weeks. The thickness of the film was about 100 μm. The desired thickness may be achieved by controlling the amount of casting solution on the weigh boat. PTH/alginate disks with a diameter of 2.0 mm were punched out from the PTH/alginate films.

BSA Films: The procedure used to prepare the PTH/alginate films was also used to prepare the BSA/alginate thin disks. Briefly, a BSA/alginate solution was prepared by mixing BSA (0.15 g) and alginate (0.25 g) in Milli-Q water (10 ml). The BSA/alginate solution was then cast into thin films and punched into BSA/alginate disks with a diameter of 2.0 mm.

Polyanhydride films: SA, CCP and PEG anhydride precursors were charged into a pre-dried tube. Alternating cycles of vacuum and nitrogen purging were repeated three times, and the vacuum was maintained inside the tube at the end. The tube was then immersed into an oil bath and the vacuum was maintained under continuous pumping. The reaction mixture was stirred vigorously and purged with dry nitrogen for about 30 seconds every fifteen minutes. At the end of the reaction, the resulting polymer melt was stored in a vial filled with nitrogen at about −20° C.

The newly synthesized polyanhydride copolymers were then heated until melted. The polyanhydride melt was then cooled down to room temperature, and compressed into films of various thickness with the pressure of $5 \times 10^7$ Pa for 5 min using Carver® Presses (Carver Inc., IN). The polyanhydride films were then punched into disks with a diameter of 3.0 mm.

Substance Delivery Device Fabrication

The inner side of PLLA cylinder was first pre-wetted with ethanol. The PTH or BSA disks and polyanhydride disks were alternately introduced into the PLLA cylinder (see, for example, FIG. 1E). In those examples including the PTH layer, the loaded amount of PTH in each layer was 50% higher than that in the layer immediately above. After the PTH or BSA and polyanhydride layers were loaded, the device was compressed with a pressure of $5 \times 10^7$ Pa for about 10 min. A PLLA solution (10% wt/v) was carefully added to fill the spaces between loaded substance (PTH or BSA) layers and isolation layers (24 and 22, respectively, shown in FIG. 1E), and any gap between the stacked films and the PLLA cylinder. The device was then air purged for about 30 min to accelerate the solvent evaporation, and vacuum dried for 24 h.

In vitro BSA/PTH Release

The substance-loaded devices were immersed in 2 ml PBS (0.1 M, pH=7.4) and incubated at 37° C. After designated times, the medium was collected and replaced with equal amount of fresh PBS. The collected medium was stored at about −20° C. until analysis. The concentration of PTH in the released medium was measured using PTH (1-34) ELISA assay (Immutopics Inc., San Clemente, Calif.). The amount of released BSA was measured using a MicroBCA protein assay (Pierce, Rockford, Ill.).

In vitro PTH (1-34) Bioactivity Assay

The in vitro bioactivity of released PTH was determined by adenylate cyclase stimulation assay and cAMP binding protein assay. Briefly, rat osteosarcoma cells (ROS 17/2.8) were treated with PTH (1-34) of known concentrations, or with eluent from the PTH delivery device for designated times in calcium- and magnesium-free hanks' balanced salt solution (Invitrogen, Carlsbad, Calif.) containing 0.1% BSA and 1 mM isobutylmethylxanthine (IBMX). After incubation of the treated cells at 37° C. for about 10 min, the cAMP in cells was extracted by adding cold perchloric acid. The cAMP extracts were then neutralized by adding KOH solution, and were centrifuged to remove the precipitate. The [3H]-cAMP (ICN, Irvine, Calif.) was incubated with standards or unknowns and cAMP binding protein for 90 min on ice. The unbound [3H]-cAMP was removed by adding dextran-coated charcoal. The samples were then centrifuged and the supernatant of each tube was decanted to a scintillation tube. The radioactivity of the supernatants was determined using a liquid scintillation counter (Wallacs 1410; Wallac, Gaithersburg, Md.) and cAMP levels were calculated by the loglogit method using a standard curve.

Polyanhydrides Surface Erosion

Figure 3A:
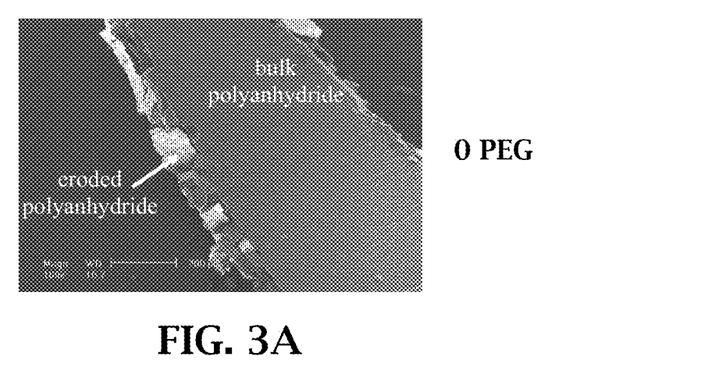
FIGS. 3A through 3C depict scanning electron microscope (SEM) micrographs of polyanhydride specimens (including polyethylene glycol (PEG), sebacic acid (SA), and 1,3-bis (carboxyphenoxy)propane (CPP)) with different compositions after erosion in 0.1M PBS at 37° C. for 24 h, where FIG. 3A includes PEG/SA/CPP=0/20/80, FIG. 3B includes PEG/SA/CPP=2.5/20/80, and FIG. 3C includes PEG/SA/CPP/=7.5/20/80.
Figure 3B:
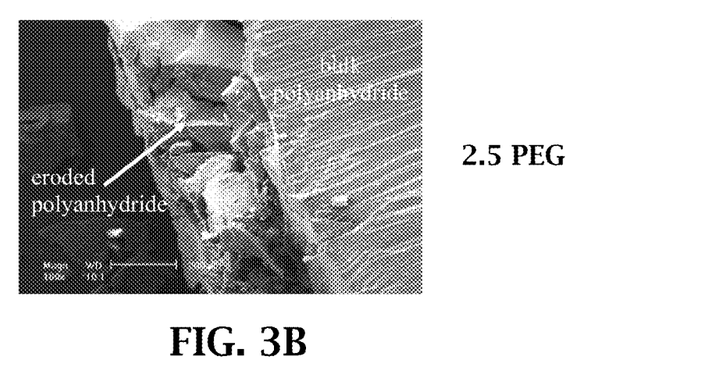
Figure 3C:
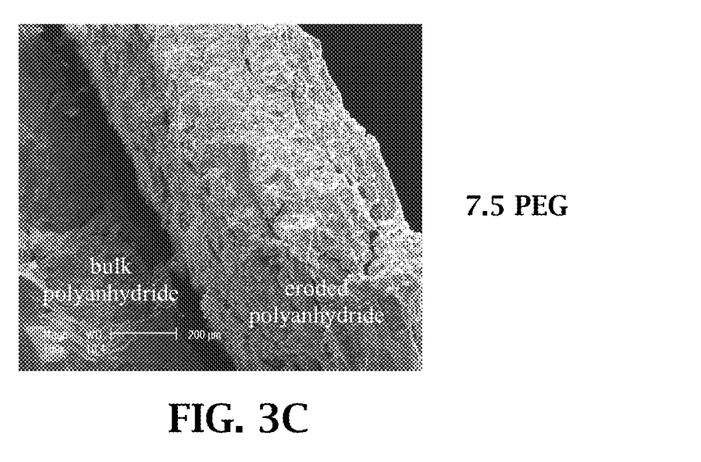

The three-component (SA, CPP and PEG) polyanhydrides showed surface erosion characteristics (see FIG. 3 series). Polyanhydrides containing PEG segments (FIGs. 3B and 3C) exhibited faster erosion rates compared to those without PEG (FIG. 3A). The erosion depth of the cylindrical polyanhydride without PEG segments (FIG. 3A) was about 100 μm after 24 h in PBS at 37° C., while the erosion depths were about 380 μm and 650 μm for polyanhydrides with 2.5% and 7.5% PEG (FIGs. 3B and 3C, respectively) in the copolymers, respectively. There were evident intervening spaces between the eroded and un-eroded portions of all surface-eroded samples. For polyanhydride with 2.5% PEG (FIG. 3B), a small portion of the particles from the eroded polyanhydride was found to be separated from the bulk of polyanhydride. As PEG content of the copolymer increased to 7.5% (FIG. 3C), virtually the entire eroded portion was detached from the un-eroded portion of the cylindrical polyanhydride. The eroded surfaces were floppy and porous. The surface roughness increased with increasing PEG content of the polyanhydride.

Pulsatile Protein Release from the Device

Figure 4:
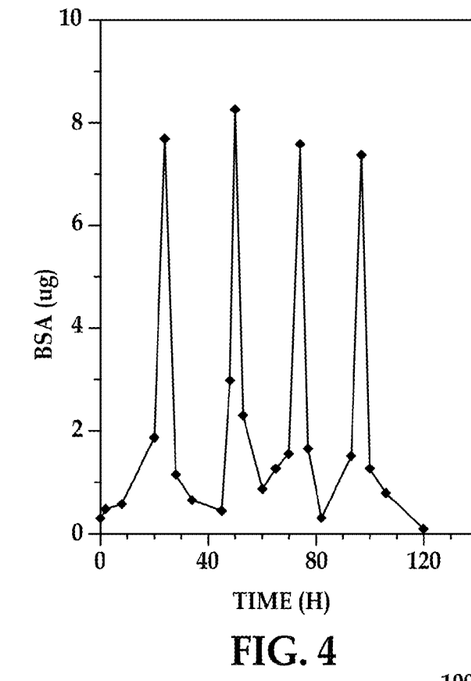
FIG. 4 is a graph depicting a pulsed release profile of bovine serum albumin (BSA) from an embodiment of the delivery device including four layers of BSA, and polyanhydride layers (with PEG amount of 1.6% in the polyanhydride copolymer) having a thickness of about 230±20 µm (n=3)

The release profile of the device including BSA layers was investigated. FIG. 4 shows four well-defined pulses with an interval of 24 h between two adjacent pulses. The released amount of BSA was almost the same for each pulse. As shown in the graph, the released amounts of BSA between pulses were very low.

Figure 5:
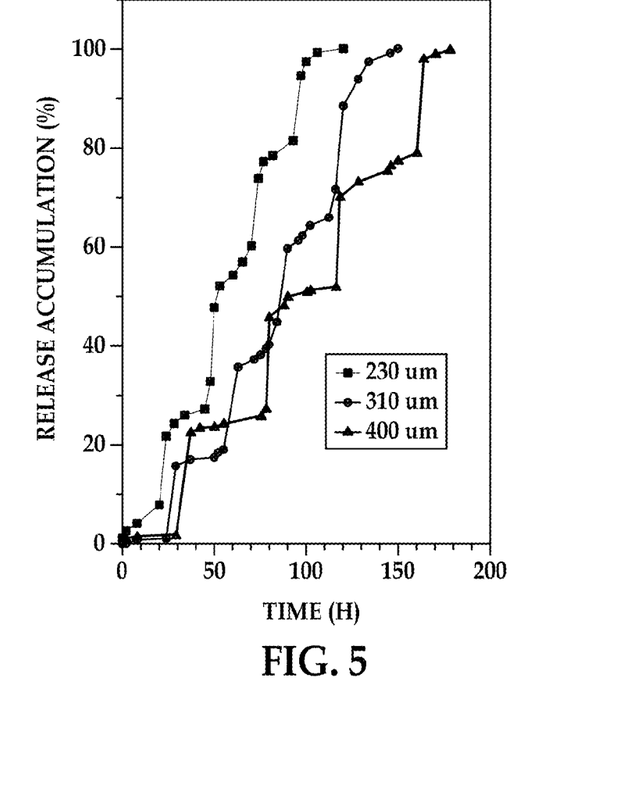
FIG. 5 is a graph depicting the release accumulation of BSA from embodiments of the delivery device having four layers of BSA, and isolation layers with different thicknesses.

It is believed that the time interval between two pulses (lag time) is controllable by the thickness of polyanhydride films, which acted as isolation layers 22. One device including BSA layers had polyanhydride films with varying thicknesses (230 μm, 310 μm, and 400 μm, respectively). The lag time increased approximately linearly with the thickness of the polyanhydride films (isolation layer 22). As shown in FIG. 5, the lag time increased from about 24 h to about 40 h when the thickness of the polyanhydride layer (with 1.6% PEG in the polyanhydride) increased from 230 μm to 400 μm.

Figure 6:
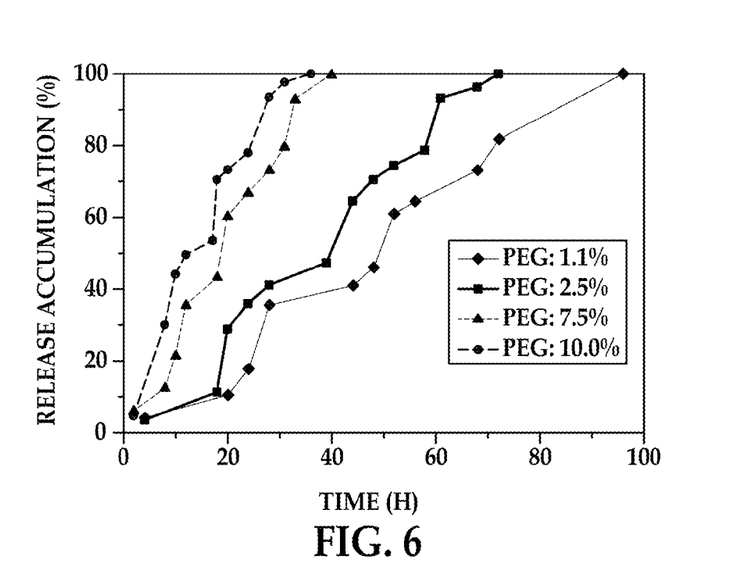
FIG. 6 is a graph depicting the cumulative release of BSA from embodiments of the delivery devices having three layers of BSA, and different compositions of polyanhydrides as isolation layer materials.

The lag time may also be controlled by polyanhydride composition (see FIG. 6). The results shown in FIG. 6 were for devices including three BSA layers with isolation layers of the same thickness, but different PEG content, therebetween. Three pulses of BSA release were observed on each cumulative release curve. The lag times of BSA release were about 24 h and 32 h for the devices with PEG contents of 1.1% and 2.5%, respectively. As the PEG content was further increased to 7.5% and 10.0%, the substance was released much faster and the lag times were about 14 h and 12 h, respectively. At these two high PEG contents, the pulses became less defined to nearly un-identifiable. BSA was released almost at a constant rate when PEG content in the polyanhydride was about 10.0%.

Figure 7:
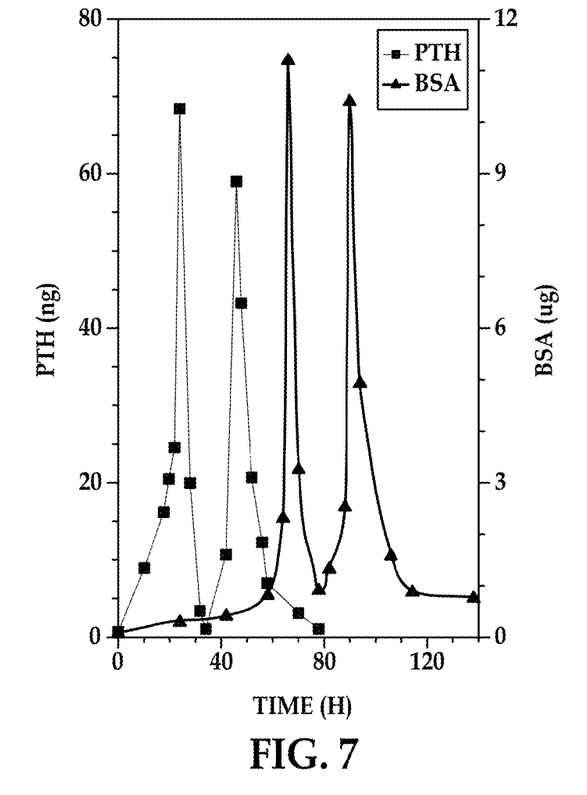
FIG. 7 is a graph depicting the pulsed release profiles of parathyroid hormone (PTH) and BSA from embodiments of the delivery device, each device including first and second substance layers loaded with PTH, third and fourth substance layers loaded with BSA, and polyanhydride isolation layers (with PEG amount of 1.6% in the polyanhydride copolymer) with a thickness of 230 µm.

The release of different substances at different time points was realized with one embodiment of the delivery device. In FIG. 7, both PTH and BSA were loaded in the same device (the first two layers were loaded with PTH, and the third and fourth layers were loaded with BSA). Two pulses of PTH were first released between 0 and 50 h, followed by two pulses of BSA released between 50 h and 100 h. The released pulses appeared at about every 24 h, as designed.

In vitro PTH Release and Bioactivity

Figure 8A:
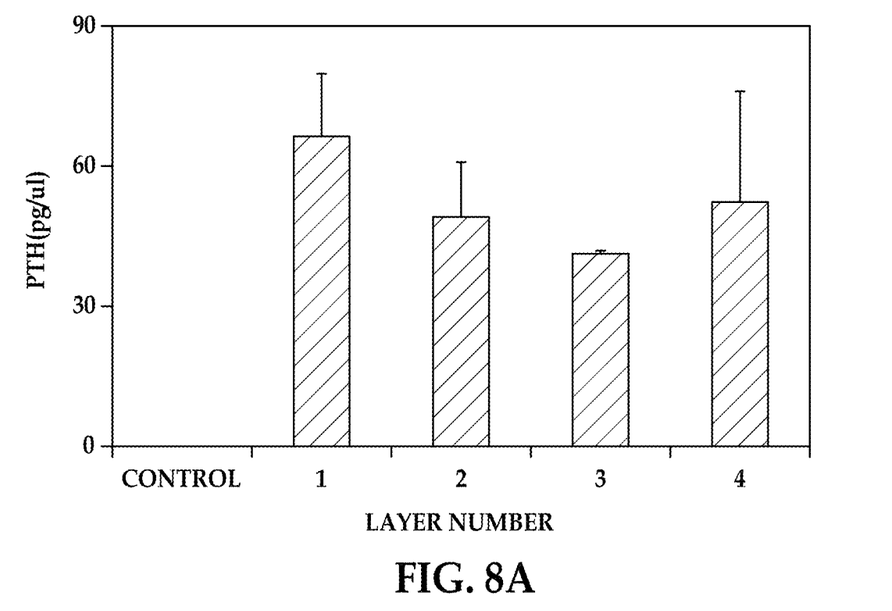
FIG. 8A is a graph depicting the PTH concentration in device eluent measured using a PTH (1-34) ELISA kit with PTH antibody coated wells, where the devices included four layers of PTH and were incubated in PBS at 37° C., the eluent was collected at 24 h, 48 h, 72 h, and 96 h, respectively, and where the concentration of PTH in the eluent of the control devices (no PTH loaded) was less than 1 pg/µl.
Figure 8B:
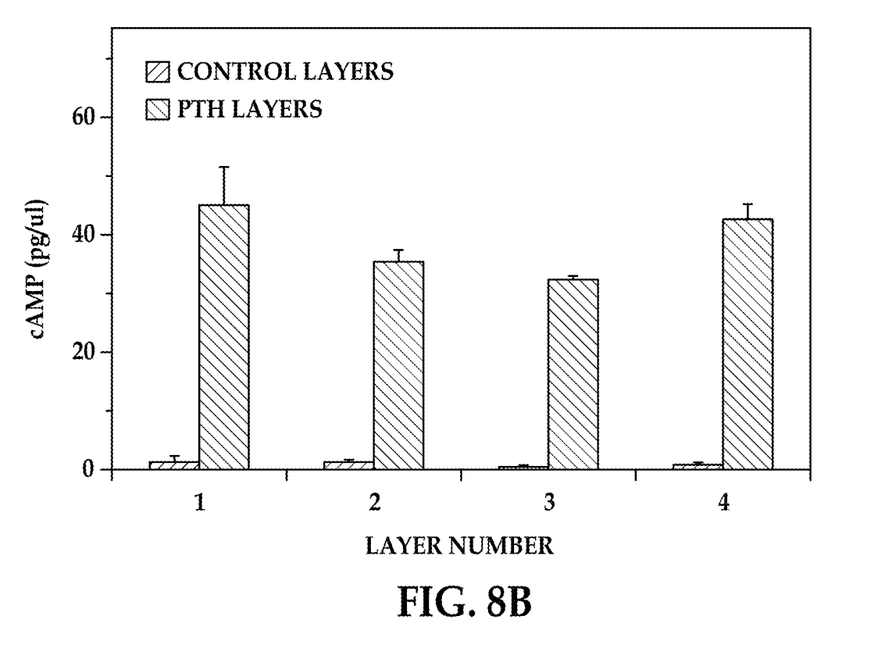
FIG. 8B is a graph depicting the biological activity (values are the mean for triplicate samples) of eluent from devices as described in FIG. 8A, the PTH receptor-mediated adenylate cyclase was stimulated by treating ROS (17/2.8) cells with known concentrations of PTH (1-34) or with devices eluent (from control layers or PTH layers) of different layers, the cAMP in the cells was extracted and a cAMP binding protein assay was performed to determine cAMP levels, and the level of cAMP in all the control devices (no PTH loaded) was less than 2 pg/µl.

Multi-pulse release of PTH from the device was also examined. FIG. 8A illustrates the amount of PTH released from each layer in the device (every pulse of release is associated with one PTH-containing layer). Similar amounts of PTH were released from each layer of the device. The bioactivity of PTH released from each layer was measured in vitro (see FIG. 8B). Based on the standard curve of PTH (positive control), the bioactivity of PTH released from the last layer was equivalent to 47.5 pg/μl PTH. Compared to the released amount of PTH from the last layer in FIG. 8A, it was calculated that 90.9% PTH was bioactive after it was released from the device. Similar results of released PTH from other layers were obtained. Therefore, it is believed that the released PTH from the delivery system retained high bioactivity.

PTH and other therapeutic agents are well known for their catabolic action resulting in bone resorption and an increase of calcium concentration in the blood. Interestingly, PTH also has anabolic action to stimulate bone formation under certain conditions. The catabolic or anabolic action of PTH (and potentially other like therapeutic agents) depends on the pattern of delivery: continuous exposure to PTH results in bone resorption, whereas intermittent administration (pulsatile release) of PTH increases bone formation. Therefore, the device 10 disclosed herein may be particularly suitable because the release of the substance may be controlled and relatively precisely modulated.

The biocompatible materials used to form the device 10 render the device 10 suitable for implantation into a human or other animal. Furthermore, the configuration and fabrication techniques used result in relatively small device 10 sizes, and the potential for further miniaturization using such techniques also exists.

The device 10 disclosed herein also advantageously prevents device leakage. If the isolation layer 22 or sealant filling has defective pores connecting or increasing diffusion between substance layers 24, body fluid (water) is likely to penetrate inside the substance layer 24 before the isolation layer 22 is eroded. This may lead to unpredictable substance release patterns. Embodiments of the device 10 aim to prevent such leakage. First, the size of substance layers 24 may be designed to be smaller than that of isolation layers 22 (see FIG. 1E), such that the contact area between the substance layers 24 and isolation layers 22 near the outer edges (i.e., areas of a higher defective probability) is decreased. Second, the sealant material is used to fill the gap between the layers 22, 24 and the container 20. Third, the device 10 may be continually compressed with constant pressure during the sealing process to reduce the possibility of air pocket formation.

The delivery device 10 disclosed herein includes, but it not limited to the following advantageous characteristics. All layers of materials (e.g., alginate, polyanhydride, PLLA) used to form the device 10 are biocompatible and biodegradable. As such, the device 10 may be implanted in vivo with minimal immuno-reaction. Furthermore, devices 10 of various shapes and sizes may be accurately fabricated using the reverse solid free form fabrication technique. Still further, embodiments of the device 10 are able to deliver more than one substance, and the substance loadings may be tailored over a broad range.

While several embodiments have been described in detail, it will be apparent to those skilled in the art that the disclosed embodiments may be modified. Therefore, the foregoing description is to be considered exemplary rather than limiting.

What is claimed is:

1. A delivery device, comprising:
    a hollow container;
    a plurality of solid polymeric layers established in the container, wherein the solid polymeric layers chosen from poly(lactide-co-glycolide) (PLGA); polyglycolic acid (PGA); poly(L-lactic acid) (PLLA); polyanhydrides; poly(ortho ethers); polycaprolactone; poly(hydroxy butyrate); poly(phosphoesters); poly(propylene fumarate); polyphosphazenes; polycarbonates; polyurethane; copolymers thereof; a copolymer of a sebacic acid anhydride precursor, a 1,3-bis(carboxyphenoxy) propane anhydride precursor, and a poly(ethylene glycol) anhydride precursor; and combinations thereof; and
    a solid layer including a film forming material and a predetermined substance incorporated into the film forming material, the solid layer being established between each of the plurality of solid polymeric layers, the film forming material being chosen from alginate; polyethylene glycol; collagen; gelatin; hyaluronic acid; starch; glycogen; cellulose; caragena; dextran; chitin; chitosan; pectin; heparan; heparan sulfate; and combinations thereof;
whereby degradation of the solid polymeric layers and release of the predetermined substance occur intermittently
wherein the surface area of the solid layer in contact with the solid polymeric layer is smaller than the surface area of the solid polymeric layer such that a gap exists between the plurality of solid polymeric layers at an outer edge of the solid layer; and the delivery device further includes a sealant material introduced into the gap.

2. The delivery device as defined in claim 1 wherein the delivery device contains a plurality of solid layers including a predetermined substance, and wherein the predetermined substance for one of the plurality of solid layers is the same or different than the predetermined substance for an other of the plurality of solid layers.

3. The delivery device as defined in claim 1 wherein the predetermined substance is selected from drugs, vaccines, proteins, peptides, growth factors, hormones, DNAs, RNAs, biological molecules, non-biological molecules, and combinations thereof.

4. The delivery device as defined in claim 1 wherein each of the solid polymeric layers is a surface-erosion polymer.

5. The delivery device as defined in claim 1 wherein the delivery device contains a plurality of solid layers including a predetermined substance, and wherein an amount of the predetermined substance in one of the plurality of solid layers is higher than an amount of the predetermined substance in an other of the plurality of solid layers.

6. The delivery device as defined in claim 1 wherein the predetermined substance includes at least two different substances.

7. A method for forming a delivery device, comprising:
providing a hollow container; and
establishing, in the hollow container, alternating solid layers of i) polymer and ii) a film forming material and a predetermined substance incorporated into the film forming material, wherein the polymer is chosen from poly(lactide-co-glycolide) (PLGA); polyglycolic acid (PGA); poly(L-lactic acid) (PLLA); polyanhydrides; poly(ortho ethers); polycaprolactone; poly(hydroxy butyrate); poly(phosphoesters); poly(propylene fumarate); polyphosphazenes; polycarbonates; polyurethane; copolymers thereof; a copolymer of a sebacic acid anhydride precursor, a 1,3-bis(carboxyphenoxy) propane anhydride precursor, and a poly(ethylene glycol) anhydride precursor; and combinations thereof; and wherein the film forming material is chosen from alginate; polyethylene glycol; collagen; gelatin; hyaluronic acid; starch; glycogen; cellulose; caragena; dextran; chitin; chitosan; pectin; heparan; heparan sulfate; and combinations thereof,
wherein the surface area of the solid layer in contact with the solid polymeric layer is smaller than the surface area of the solid polymeric layer such that a gap exists between the plurality of solid polymeric layers at an outer edge of the solid layer; and the delivery device further includes a sealant material introduced into the gap.

8. The method as defined in claim 7 wherein providing the hollow container is accomplished by a reverse solid free form fabrication technique.

9. The method as defined in claim 8 wherein providing the hollow container is accomplished by:
printing a mold of the hollow container, the mold having a bottom, an exterior layer, an interior layer, and a layer intermediate the exterior and interior layers; removing the intermediate layer;
establishing a material that forms the hollow container between the interior and exterior layers and adjacent the bottom; and
removing the interior layer, the exterior layer, and the bottom, thereby forming the hollow container of the material.

10. The method as defined in claim 7 wherein prior to establishing the alternating layers, the method further comprises forming the polymer layer by:
melting the copolymer of the sebacic acid anhydride precursor, the 1,3-bis(carboxyphenoxy) propane anhydride precursor, and the poly(ethylene glycol) anhydride precursor; and
compressing the melted copolymer into a layer as it cools.

11. The method as defined in claim 7, wherein prior to establishing alternating layers, the method further comprises forming the film forming material and predetermined substance layer by:
mixing the predetermined substance with the film forming material, thereby forming a solution; and
casting the solution onto a removable substrate.

12. The method as defined in claim 7 wherein prior to establishing the alternating layers, the method further comprises pre-wetting an inner side of the hollow container with a liquid.

13. The method as defined in claim 7, further comprising:
compressing the delivery device with a predetermined pressure;
adding a polymer to substantially fill any gaps within the hollow container;
purging the delivery device; and
drying the delivery device.

14. An implantable delivery device, comprising:
a hollow container selected from poly(lactide-co-glycolide) (PLGA), polyglycolic acid (PGA), polyanhydrides, poly(ortho ethers), polycaprolactone, poly(hydroxy butyrate), poly(phosphoesters), poly(propylene fumarate), polyphosphazenes, polycarbonates, polyethylene, polyurethane, copolymers thereof, or combinations thereof;
a plurality of solid polymeric layers established in the container, wherein the solid polymeric layers is selected from poly(lactide-co-glycolide) (PLGA); polyglycolic acid (PGA); poly(L-lactic acid) (PLLA); polyanhydrides; poly(ortho ethers); polycaprolactone; poly(hydroxy butyrate); poly(phosphoesters); poly(propylene fumarate); polyphosphazenes; polycarbonates; polyurethane; copolymers thereof; a copolymer of a sebacic acid anhydride precursor, a 1,3- bis(carboxyphenoxy) propane anhydride precursor, and a poly(ethylene glycol) anhydride precursor; and combinations thereof; and
a solid layer including a film forming material and a predetermined substance incorporated into the film forming material, the solid layer being established between each of the plurality of solid polymeric layers, the film forming material being chosen from alginate; polyethylene glycol; collagen; gelatin; hyaluronic acid; starch; glycogen; cellulose; caragena; dextran; chitin; chitosan; pectin; heparan; heparan sulfate; and combinations thereof;
whereby degradation of the solid polymeric layers and release of the predetermined substance occur intermittently wherein the surface area of the solid layer in contact with the solid polymeric layer is smaller than the surface area of the solid polymeric layer such that a gap exists between the plurality of solid polymeric layers at an outer edge of the solid layer; and the delivery device further includes a sealant material introduced into the gap.

15. The delivery device as defined in claim 1 wherein the film forming material is chosen from alginate; collagen; hyaluronic acid; glycogen; caragena; chitosan; pectin; heparin; heparin sulfate; and a combination thereof.

* * * * *

UNITED STATES PATENT AND TRADEMARK OFFICE
CERTIFICATE OF CORRECTION

| | | |
|---|---|---|
| PATENT NO. | : 8,623,397 B2 | Page 1 of 1 |
| APPLICATION NO. | : 12/101993 | |
| DATED | : January 7, 2014 | |
| INVENTOR(S) | : Ma et al. | |

It is certified that error appears in the above-identified patent and that said Letters Patent is hereby corrected as shown below:

In the Specification

Column 1, lines 11-21, "Statement Regarding Federally Sponsored Research and Development," should read --This invention was made with government support under NNC04AA21A awarded by the National Aeronautics and Space Administration (NASA), and under DE015384 awarded by the National Institutes of Health (NIH). The Government has certain rights in the invention.--

Signed and Sealed this
Seventh Day of October, 2014

Michelle K. Lee
*Deputy Director of the United States Patent and Trademark Office*